(12) United States Patent
Peyman

(10) Patent No.: US 6,197,019 B1
(45) Date of Patent: Mar. 6, 2001

(54) UNIVERSAL IMPLANT BLANK FOR MODIFYING CORNEAL CURVATURE AND METHODS OF MODIFYING CORNEAL CURVATURE THEREWITH

(76) Inventor: Gholam A. Peyman, 8654 Pontchartrain Blvd. Unit 1, New Orleans, LA (US) 70124

( * ) Notice: Subject to any disclaimer, the term of this patent is extended or adjusted under 35 U.S.C. 154(b) by 0 days.

(21) Appl. No.: 09/260,570

(22) Filed: Mar. 2, 1999

Related U.S. Application Data

(63) Continuation of application No. 08/845,448, filed on Apr. 25, 1994, now Pat. No. 5,919,185.

(51) Int. Cl.$^7$ ................................................ A61N 5/06
(52) U.S. Cl. ................................ 606/5; 606/4; 523/5.11
(58) Field of Search ................................ 606/4, 5; 623/5

(56) References Cited

U.S. PATENT DOCUMENTS

| | | |
|---|---|---|
| 4,505,855 | 3/1985 | Burns et al. . |
| 4,676,790 | 6/1987 | Kern . |
| 4,678,422 | 7/1987 | York . |
| 4,718,418 | 1/1988 | L'Esperance . |
| 4,807,623 | 2/1989 | Lieberman . |
| 4,840,175 | 6/1989 | Peyman . |
| 4,994,058 | 2/1991 | Raven et al. . |
| 5,123,921 | 6/1992 | Werblin et al. . |
| 5,196,026 | 3/1993 | Barrett et al. . |
| 5,336,261 | 8/1994 | Barrett et al. . |
| 5,391,201 | 2/1995 | Barrett et al. . |
| 5,647,865 | 7/1997 | Swinger . |

OTHER PUBLICATIONS

Jose I. Barraquer, "Keratomileusis and Keratophakia in the Surgical Correction of Apkakia", Chapter 7 of Cataract Surgery and Special Techniques, pp. 270–289 (published prior to 1996).

*Primary Examiner*—Michael Buiz
*Assistant Examiner*—Julian W. Woo
(74) *Attorney, Agent, or Firm*—Roylance, Abrams, Berdo & Goodman, LLP

(57) ABSTRACT

A universally sized blank made of organic or synthetic material that can be placed on an exposed inner surface of a live cornea and ablated with a laser beam to be altered to a particular shape. A flap-like portion of the live cornea is removed to expose an inner surface of the cornea, and the blank is positioned on the exposed inner surface of the eye. A laser beam is directed onto certain portions of the blank that are selected based on the type of ametropic condition (i.e., myopia, hyperopia or astigmatism) of the eye needing correction, so that the laser beam ablates those portions and thus reshapes the blank. The laser beam can also be directed onto certain portions of the laser surface of the cornea to ablate those surfaces of the cornea. The flap-like portion of the cornea is repositioned over the remaining portion of the blank, so that the remaining portion of the blank influences the shape of the reattached flap-like portion of the cornea and thus modifies the curvature of the cornea.

20 Claims, 16 Drawing Sheets

UNIVERSAL IMPLANT BLANK FOR MODIFYING CORNEAL CURVATURE AND METHODS OF MODIFYING CORNEAL CURVATURE THEREWITH

This is a continuation application of U.S. patent application Ser. No. 08/845,448 filed Apr. 25, 1997, now U.S. Pat. No. 5,919,185, the entire contents of which is incorporated herein by reference.

BACKGROUND OF THE INVENTION

1. Field of the Invention

The present invention relates to a universal blank which is used to modify the curvature of a live cornea when implanted therein. The blank is made of synthetic or organic material and is shaped to the appropriate configuration while supported on an exposed inner surface of the cornea.

2. Description of the Related Art

A normal emetropic eye includes a cornea, lens and retina. The cornea and lens of a normal eye cooperatively focus light entering the eye from a far point, i.e., infinity, onto the retina. However an eye can have a disorder known as ametropia, which is the inability of the lens and cornea to focus the far point correctly on the retina. Typical types of ametropia are myopia, hypermetropia or hyperopia, and astigmatism.

A myopic eye has either an axial length that is longer than that of a normal emetropic eye, or a cornea or lens having a refractive power stronger than that of the cornea and lens of an emetropic eye. This stronger refractive power causes the far point to be projected in front of the retina.

Conversely, a hypermetropic or hyperopic eye has an axial length shorter than that of a normal emetropic eye, or a lens or cornea having a refractive power less than that of a lens and cornea of an emetropic eye. This lesser refractive power causes the far point to be focused in back of the retina.

An eye suffering from astigmatism has a defect in the lens or shape of the cornea. Therefore, an astigmatic eye is incapable of sharply focusing images on the retina.

A common method of correcting myopia is to place a "minus" or concave lens in front of the eye in order to decrease the refractive power of the cornea and lens. In a similar manner, hypermetropic or hyperopic conditions can be corrected to a certain degree by placing a "plus" or convex lens in front of the eye to increase the refractive power of the cornea and lens. Lenses having other shapes can be used to correct astigmatism. The concave, convex or other shaped lenses are typically configured in the form of glasses or contact lenses. This technique, which involves the placement of lenses in front of the eye, is known as photorefractive keratectomy.

Although photorefractive keratectomy can be used to correct vision in eyes suffering from low myopia up to 6 diopters, or in eyes suffering from hypermetropic, hyperopic or astigmatic conditions which are not very severe, that method is ineffective in correcting vision in eyes suffering from sever forms of ametropia. For example, photorefractive keratectomy is ineffective in correcting high myopia of 6 diopters or greater, and is also ineffective in correcting severe astigmatism and severe forms of hypermetropia or hyperopia.

However, surgical techniques exist for correcting these more severe forms of ametropia to a certain degree. For example, in a technique known as myopic keratomileusis, a microkeratome is used to cut away a portion of the front of the live cornea from the main section of the live cornea. The cut portion of the cornea is frozen and placed in a cryolathe where it is cut and reshaped. Altering the shape of the cut portion of the cornea changes the refractive power of this cut portion, which thus affects the location at which light entering the cut portion of the cornea is focused. The reshaped cut portion of the cornea is then reattached to the main portion of the live cornea. Hence, it is intended that the reshaped cornea will change the position at which the light entering the eye through the cut portion is focused, so that hopefully the light is focused on the retina, thus remedying the ametropic condition.

The myopic keratomileusis technique is known to be effective in curing myopic conditions within a range of 6 to 18 diopters. However, the technique is impractical because it employs very complicated and time consuming freezing, cutting and thawing processes. Furthermore, the technique is ineffective in correcting myopic conditions greater than 18 diopters.

Keratophakia is another known surgical technique for correcting sever ametropic conditions of the eye by altering the shape of the eye's cornea. In this technique an artificial organic or synthetic lens is implanted inside the cornea to thereby alter the shape of the cornea and thus change its refractive power. Accordingly, as with the myopic keratomileusis technique, it is desirable that the shape of the cornea be altered to a degree allowing light entering the eye to be focused correctly on the retina.

However the keratophakia technique is impractical, complicated, and expensive because it requires manufacturing or cutting a special lens prior to its insertion into the cornea. Hence, a surgeon is required to either maintain an assortment of many differently shaped lenses, or alternatively, must have access to expensive equipment, such as a cyrolathe, which can be used to cut the lens prior to insertion into the cornea.

Surgical techniques involving the use of ultraviolet and shorter wavelength lasers to modify the shape of the cornea also are known. For example, excimer lasers, such as those described in U.S. Pat. No. 4,840,175 to Peyman, which emit pulsed ultraviolet radiation, can be used to decompose or photoablate tissue in the live cornea so as to reshape the cornea.

Specifically, a laser surgical technique known as laser in situ keratomycosis (LASIK) has been previously developed by the present inventor. In this technique, a portion of the front of a live cornea can be cut away in the form of a flap having a thickness of about 160 microns. This cut portion is removed from the live cornea to expose an inner surface of the cornea. A laser beam is then directed onto the exposed inner surface to ablate a desired amount of the inner surface up to 150–180 microns deep. The cut portion is then reattached over the ablated portion of the cornea and assumes a shape conforming to that of the ablated portion.

However, because only a certain amount of cornea can be ablated without the remaining cornea becoming unstable or experiencing outbulging (eklasia), this technique is not especially effective in correcting very high myopia. That is, a typical live cornea is on average about 500 microns thick. The laser ablation technique requires that at least about 200 microns of the corneal stroma remain after the ablation is completed so that instability and outbulging does not occur. Hence, this procedure cannot be effectively used to correct high myopia of greater than 15 diopters because in order to reshape the cornea to the degree necessary to alter its refractive power so as to sufficiently correct the focusing of the eye, too much of the cornea would need to be ablated.

Examples of known techniques for modifying corneal curvature, such as those discussed above, are described in U.S. Pat. No. 4,994,058 to Raven et al., U.S. Pat. No. 4,718,418 to L'Esperance, U.S. Pat. No. 5,336,261 to Barrett et al., U.S. Pat. No. 4,840,175 to Peyman, and a publication by Jose I. Earraquer, M. D. entitled "Keratomileusis and Keratophakia in the Surgical Correction of Aphakia".

A continuing need therefore exists for improved methods to correct very severe ametropic conditions.

SUMMARY OF THE INVENTION

Accordingly, a primary object of the present invention is to provide a device which can be used to modify corneal curvature without experiencing the drawbacks associated with the known techniques discussed above, to thus correct severe ametropic conditions.

Another object of the invention is to configure the device to be positioned on the surface of the cornea and reshaped while on the surface of the cornea so that the device need not be prefabricated or modified prior to placement on the cornea.

A further object of the invention is to provide a method for modifying the shape of a live cornea by using a device that can be placed on the surface of the live cornea and reshaped thereon.

Still a further object of the invention is to provide a method for modifying the shape of a live cornea by removing a layer of the live cornea to expose a surface underneath, placing a device on the exposed surface that can be reshaped while on the exposed surface, reshaping the device, and repositioning the layer over the remaining portion of the reshaped device so that the reshaped device influences the shape of the layer and thus the overall cornea.

The foregoing objects are basically obtained by providing a universally sized blank made of organic material, synthetic material, or a combination of organic and synthetic material, that can be placed on an exposed inner surface of a live cornea and ablated with a laser beam to be altered to a particular shape. The universally sized blank can be porous to allow oxygen and nutrients to pass there through. Also, the blank can be made from living cells such as a donor cornea of a human eye (e.g., as taken from an eye bank), or can be taken from a cultured cornea.

A flap-like portion of the live cornea is removed to expose the inner surface of the cornea. The blank is positioned on the exposed inner surface of the cornea, and a laser beam is directed onto certain portions of the blank to ablate those portions and thus reshape the blank based on the type of ametropic condition (i.e., myopia, hyperopia or astigmatism) of the eye needing correction. The flap-like portion of the cornea is then repositioned over the remaining portion of the blank, so that the remaining portion of the blank influences the shape of the reattached flap-like portion of the cornea, thus modifying the curvature of the surface of the cornea. The universal blank can therefore be used to correct severe ametropic conditions, such as high myopia up to 35 diopters.

Other objects, advantages, and salient features of the present invention will become apparent from the following detailed description, which, taken in conjunction with the attached drawings, discloses preferred embodiments of the invention.

BRIEF DESCRIPTION OF THE DRAWINGS

Referring now to the drawings which form a part of the original disclosure.

DETAILED DESCRIPTION OF THE PREFERRED EMBODIMENTS

Figure 1:
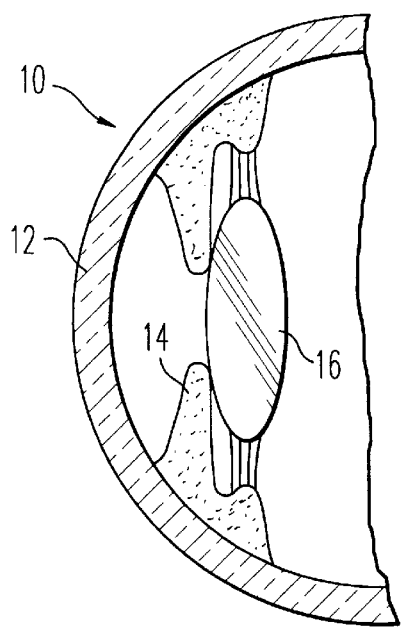
FIG. 1 is a side elevational view in section taken through the center of an eye showing the cornea, pupil and lens.

FIG. 1 is a side elevational view in section taken through the center of an eye 10 which includes a cornea 12, a pupil 14 and a lens 16. If the cornea 12 and lens 16 do not cooperatively focus light correctly on the retina (not shown) of the eye to thus provide adequate vision, the curvature of the cornea can be modified to correct the refractive power of the cornea and thus correct the manner in which the light is focused with respect to the retina.

Figure 2:
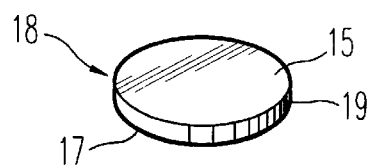
FIG. 2 is a perspective view of an embodiment of a universal blank according to the present invention.
Figure 3:
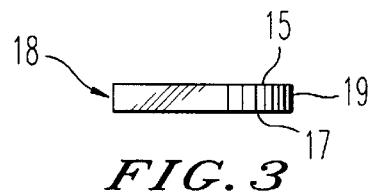
FIG. 3 is a front elevational view of the embodiment shown in FIG. 2.
Figure 4:
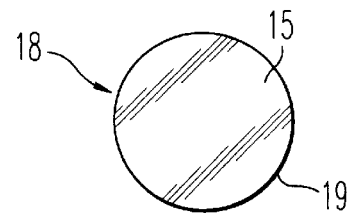
FIG. 4 is a top elevational view of the embodiment shown in FIG. 2.

A universal blank 18 according to an embodiment of the present invention is illustrated in FIGS. 2–4. As shown, the universal blank according to this embodiment is disk-shaped and has a uniform or substantially uniform thickness throughout, as illustrated specifically in FIG. 3. Specifically, the blank 18 has a first planar or substantially planar surface 15, a second planar or substantially planar surface 17, and a periphery 19. The surfaces 15 and 17 are arranged parallel or substantially parallel to each other with the periphery 19 being perpendicular or substantially perpendicular to one or both surfaces 15 and 17. Of course, the surfaces 15 and 17 and the periphery 19 need not be uniform but could have recesses, projections, raised portions, or any variation in shape and texture. Preferably, the universal blank 18 has a diameter of about 4 to about 9 mm and a thickness of between about 20 to about 500 microns. Of course, the diameter and thickness of the disk-shaped universal blank 18 can be of any practical size as would be appreciated by one skilled in the art. Furthermore, the universal blank need not be disk-shaped although it is preferred as shown in the embodiment of FIGS. 2–4, but can be frusto-conical, oval, square, rectangle, or any practical shape as would be readily appreciated by one skilled in the art.

The blank 18 is preferably made of synthetic material, organic material, or a combination of both synthetic and organic material, that permits all or substantially all light having a wavelength in the visible spectrum to pass through, but absorbs all or substantially all light having a wavelength in a laser light spectrum. For example, the blank 18 can be made of collagen, copolymer collagen, polyethylene oxide or hydrogel, or cross-linked organic material such as collagen, hyaluronic acid, mucopolysacoharide or glycoprotein, to name a few. The blank 18 is porous to allow oxygen and nutrients to pass therethrough. Also, the blank 18 can be made from a donor cornea of a human eye, or can be taken from a cultured cornea. However, the blank 18 is not limited to those materials, and can be made of any suitable material, such as those disclosed in U.S. Pat. No. 4,994,058 to Raven et al., U.S. Pat. No. 4,718,418 to L'Esperance, U.S. Pat. No. 5,336,261 to Barrett et al., U.S. Pat. No. 4,840,175 to Peyman, and a publication by Jose I. Barraquer, M.D. entitled "Keratomileusis and Keratophakia in the Surgical Correction of Aphakia", the disclosures of which are hereby incorporated by reference herein.

Figure 5:
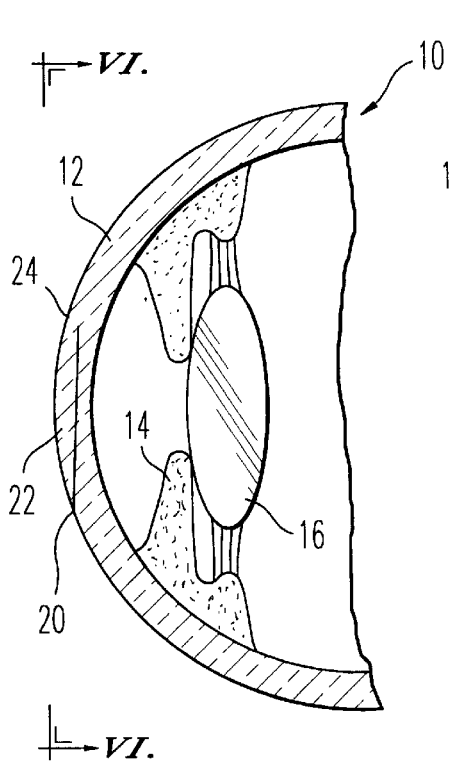
FIG. 5 is a side elevational view in section taken through the center of an eye showing formation of a flap-like structure at the front of the cornea.

The blank 18 is configured to be placed directly on an exposed inner surface of the cornea of the eye. In order to expose this inner surface of the cornea of the eye, a thin layer of the live cornea must be removed. To remove the layer of the cornea, a procedure is performed in which, for example, an incision 20 is made in the front portion of the cornea, as shown in FIG. 5. This incision 20 is made so as to separate thin layer 22 of the cornea from the remaining portion of the cornea 12. The incision can be made with a scalpel, keratome, excimer laser, or any type of surgical cutting instrument known to one skilled in the art. The layer 22 can also be separated from the surface of the live cornea by any other method which may not involve making an actual incision in the cornea as may be appreciated by one skilled in the art.

Figure 6:
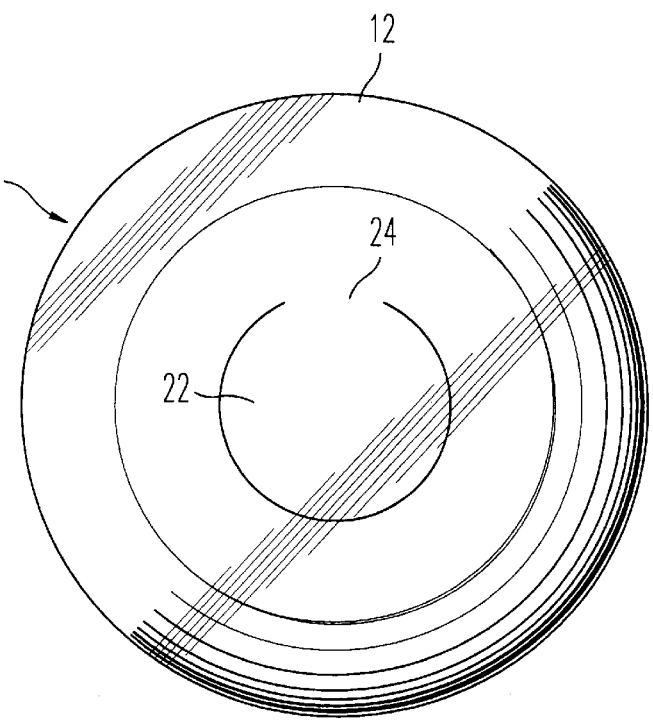
FIG. 6 is a front elevational view of the cornea and flap-like structure as taken along lines VI—VI in FIG. 5.
Figure 7:
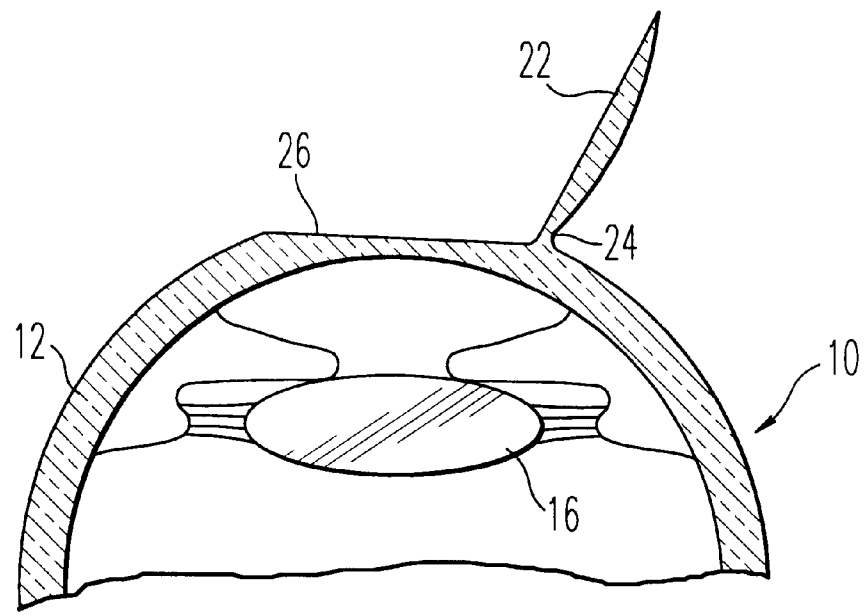
FIG. 7 is a side elevational view in section taken through the center of an eye and showing the flap-like section positioned to expose an inner surface of the cornea.

The layer 22 of the cornea can be completely removed from the remaining portion of the cornea 12. However, as shown in FIGS. 5 and 6, it is preferable that the layer 22 of the cornea remain attached to the main portion of the live cornea 12 by an attaching or hinging portion 24. Accordingly, as shown in FIG. 7, the layer 22 of the cornea is formed as a flap-like layer that is pivotally moveable about the attaching portion 24 to expose an inner surface 26 of the cornea. The layer 22 typically can be of any practical thickness, for example, 160 microns.

The universal blank 18 is then used to modify the curvature of the cornea in the following manner.

Figure 8:
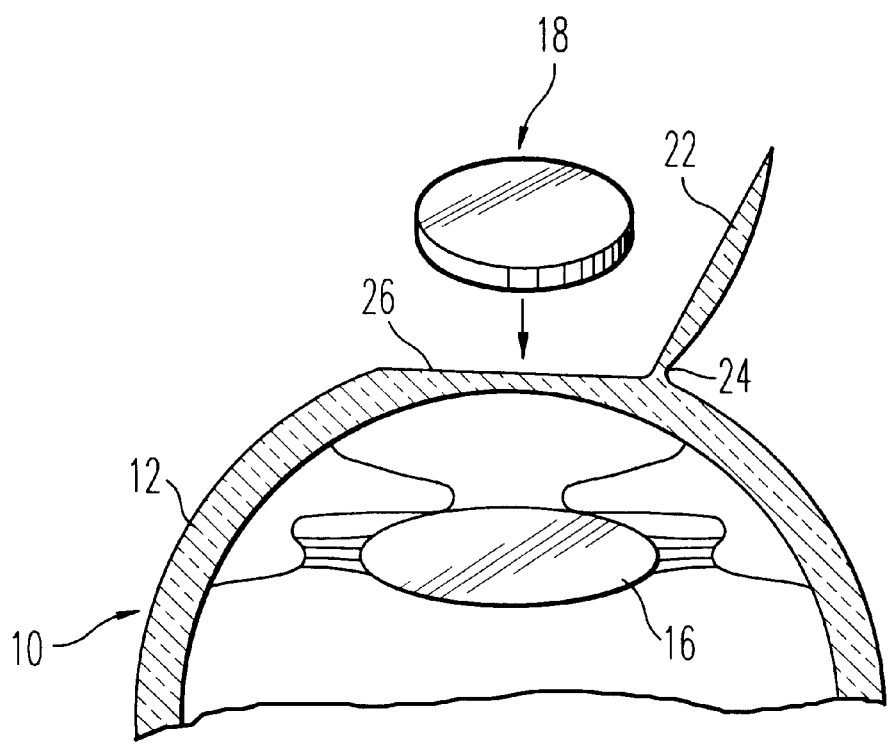
FIG. 8 is an enlarged side elevational view in section taken through the center of an eye and showing placement of the embodiment of the universal blank shown in FIG. 2 on the exposed surface of the cornea.
Figure 9:
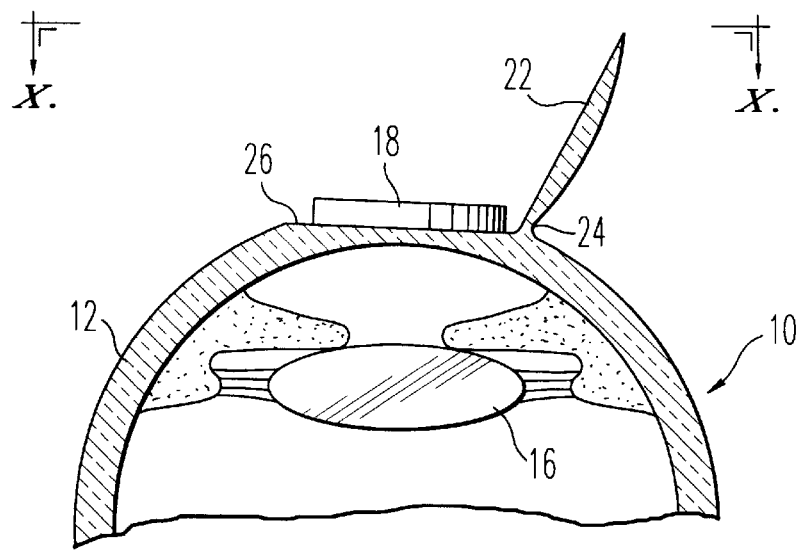
FIG. 9 is an enlarged side elevational view in section taken through the center of an eye and illustrating the universal blank shown in FIG. 2 positioned on the exposed surface of the cornea.

As shown in FIGS. 8 and 9, the flap-like layer 22 is positioned so as to expose the inner surface 26 of the cornea.

Figure 10:
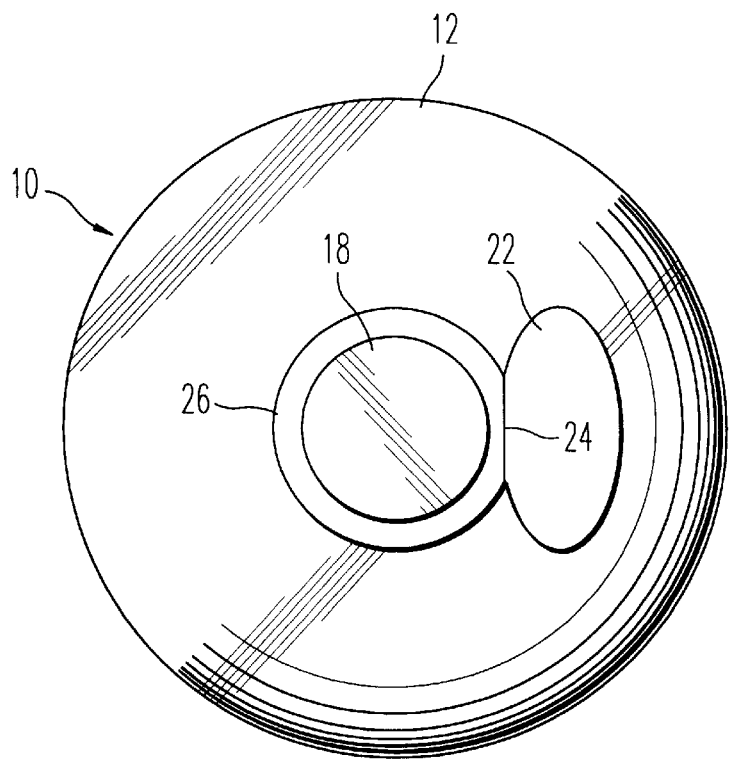
FIG. 10 is a front elevational view of the cornea with the universal blank present on the exposed surface thereof as taken along lines X—X in FIG. 9.
Figure 11:
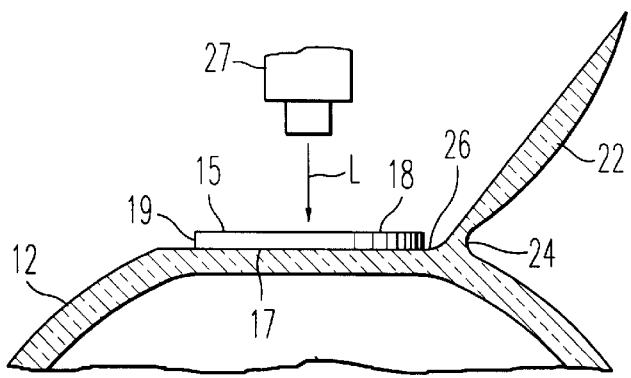
FIG. 11 is an enlarged side elevational view in section taken through the center of the eye showing the cornea and the irradiation of a laser beam on the universal blank positioned on the exposed surface of the cornea.

The blank 18 is then positioned on the exposed surface of the cornea at a position deemed suitable by the person performing the cornea modifying technique. Typically, as shown in FIG. 10, the blank 18 is positioned centrally or substantially centrally on the exposed surface 26 with the central longitudinal axis of the blank substantially coincident with the central optical axis of the eye. Of course, the blank 18 need not be positioned centrally on the exposed surface 26 as shown, but rather, its central longitudinal axis can be offset from the central optical axis of the eye.

Once positioned on the exposed surface 26 of the cornea 12, the shape of the universal blank can be modified sufficiently to influence the shape of the flap-like layer 22 and to thus change the refractive power of the flap-like layer sufficiently to correct the abnormality of the eye 10. Generally, every 10 micron change in curvature of the cornea will change the refractive power of the cornea by 1 diopter.

For example, as shown in FIGS. 11–14, a laser beam L is directed to the first upper surface 15 of the blank 18 that is opposite to the second lower surface 17 of the blank 18 that is supported on the exposed surface 26 of the cornea 12. The laser beam L can be emitted from any type of laser 27 typically used in eye surgery methods, such as an excimer laser 27 or the like as described in U.S. Pat. No. 4,840,175.

Figure 12:
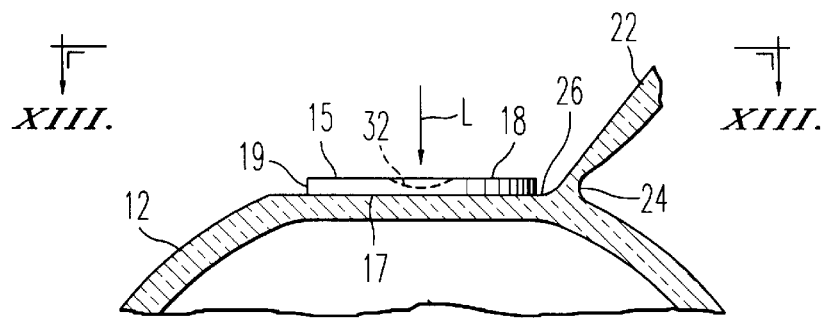
FIG. 12 illustrates ablation of the center of the universal blank by the laser beam.

As shown in FIG. 12, the laser beam L will begin to ablate or erode an area 32 of the blank 18 to which the laser beam is directed. Again, the area of the blank 18 to which the laser beam L is directed and which is ablated is selected to remedy a specific type of abnormality from which the eye is suffering.

Figure 13:
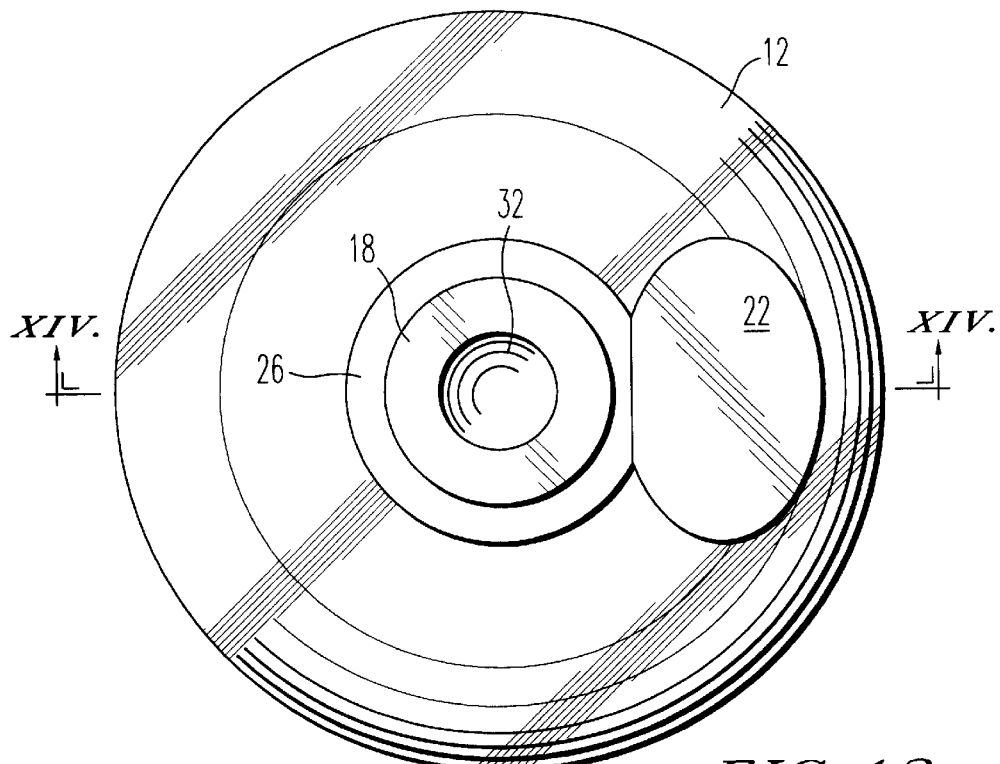
FIG. 13 is a reduced front elevational view of the ablated universal blank taken along lines XIII—XIII in FIG. 12.

For example, if the blank is being used to correct a hyperopic or hypermetropic condition, the laser beam L will be directed toward a central area 32 of the blank 18 so as to ablate that central area 32. As shown in FIG. 13, for example, the blank 18 is disk-shaped, and the area 32 that is ablated is circular in top plan view and is at least initially in the form of a substantially hemispheric recess. Of course, the shape of the ablated area can be any desired shape necessary to effect correction of the particular abnormality of the eye.

As stated previously, the blank 18 is made of a material that will absorb all or substantially all light having a wavelength within the laser light spectrum. Therefore, when the laser beam L is irradiated onto the blank 18, none or substantially none of the laser beam will pass through the blank 18 to ablate any portion of the cornea 12. However, as also previously stated, the material of the blank 18 will allow all or substantially all light having a wavelength within the visible light spectrum to pass therethrough.

Figure 14:
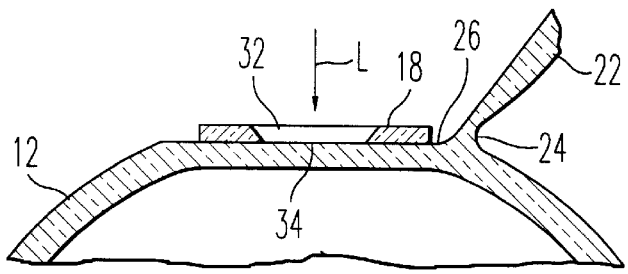
FIG. 14 is an enlarged cross-sectional view of the blank and cornea as taken along lines XIV—XIV in FIG. 13.

Hence, as shown in FIG. 14, the laser beam L can be directed to the blank 18 until the ablated central area 32 becomes a hole with a frustoconical wall which passes entirely through the blank 18 to expose a portion 34 of the surface 26 of the cornea 12. Of course, the hole can have a cylindrically or substantially cylindrically shaped wall, or any other shape as would be formed by the laser beam L. As shown in FIG. 14, none or essentially none of the surface 26 of the cornea has been ablated by the laser beam.

Figure 15:
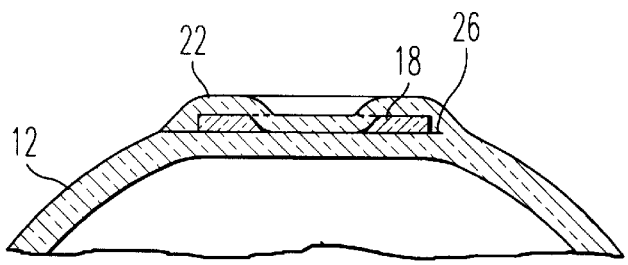
FIG. 15 is a side elevational view in section taken through the center of the eye showing the cornea and the flap-like portion reattached over the exposed surface of the cornea and the remaining portion of the ablated universal blank shown in FIG. 14.

After the laser ablation process has been completed, the flap-like layer 22 of the cornea is repositioned over the remaining portion of the blank 18 and the surface 26 of the cornea 12 as shown, for example, in FIG. 15. As illustrated, the shape of the remaining portion of the blank 18 will influence the shape of the flap-like layer 22 when the flap-like layer is repositioned over the remaining portion of the blank 18 and surface 26 of the cornea 12. Hence, the refractive power of this flap-like layer 22 will be changed due to this change in shape. The flap-like layer 22 can be reattached to the cornea 12 by any known techniques such as suturing or the like.

Because the material of the blank 18 is transparent or essentially transparent to light having a wavelength within the visible light spectrum, visible light will pass through the remaining portion to the blank 18 and enter the eye 12. However, because the reshaped flap-like layer 22 has a different refractive power, the flap-like layer 22 will refract the light passing therethrough differently than prior to the reshaping. Therefore, in cooperation with the lens 16 (see FIG. 1), this reshaped layer 22 will focus the light in the appropriate manner on the retina, thus correcting the ametropic condition of the eye.

It is further noted that the laser 27 can be used to reduce the overall thickness of the blank 18 prior to shaping the blank. For instance, the blank 18 can initially be about 500 microns thick for ease of handling. Then, once the blank 18 is positioned on the exposed inner surface of the cornea in the manner described above, the inner beam L can be directed to the upper surface 15 of the blank so as to reduce the overall thickness of the blank 18 as desired. Hence, a 500 micron thick blank can be reduced, for example, to about 100 microns or any suitable thickness by the laser beam L before the laser beam L is used to sculpt the blank 18 to a particular shape as shown, for example, in FIGS. 11–15.

Figure 16:
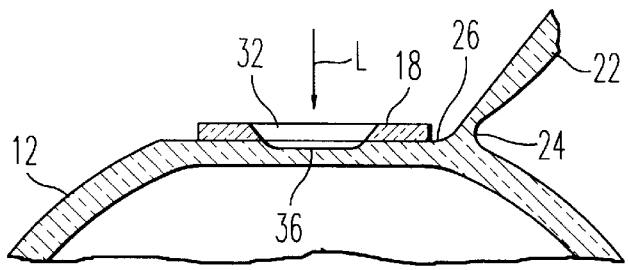
FIG. 16 is a side elevational view in section taken through the center of the eye illustrating ablation of the universal blank as well as a portion of the cornea below the blank by the laser beam.

Additionally, based on the severity of the abnormality from which the eye is suffering, it may be determined that the surface of the cornea must be reshaped more extensively. In this event, as shown in FIG. 16, the laser beam L can be irradiated onto the area 32 of the blank 18 until the area 32 of the blank 18 is completely ablated by the laser beam and becomes a hole that passes entirely through the blank 18. Afterward, the laser beam L is directed onto the exposed portion of the surface 26 of the cornea so as to ablate a portion 36 of that surface.

Figure 17:
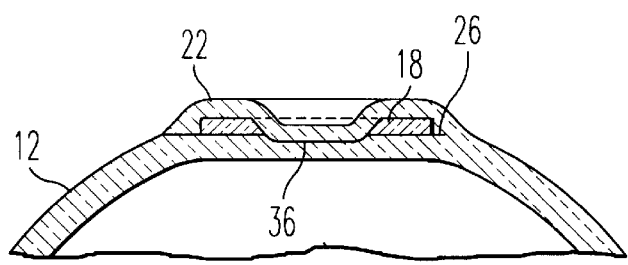
FIG. 17 is a side elevational view in section taken through the center of the eye illustrating the flap-like portion repositioned over the remaining portion of the blank and ablated portion of the cornea.
Figure 18:
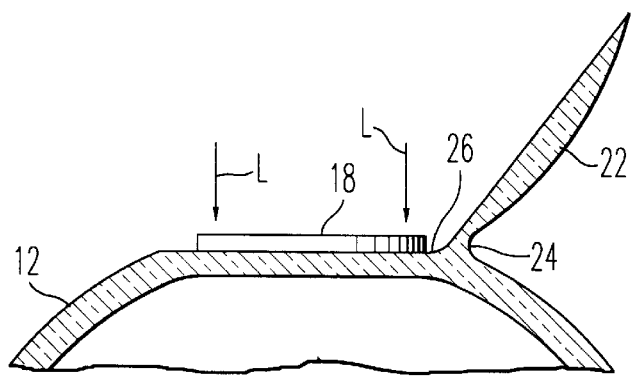
FIG. 18 is a side elevational view in section taken through the center of the eye showing the cornea and the irradiation of a laser beam on other peripheral portions or the universal blank which is positioned on the exposed surface of the cornea.

Accordingly, as shown in FIG. 17, when the flap-like layer is repositioned over the remaining portion of the blank 18 and the surface 26 of the cornea 12, the ablated portion 36 of the surface of the cornea 26 will also influence the shape of the repositioned flap-like layer 22. By using this technique, it is not necessary that the thickness of the blank 18 be changed in order to provide a more substantial change in the shape of the flap-like layer 22.

Figure 19:
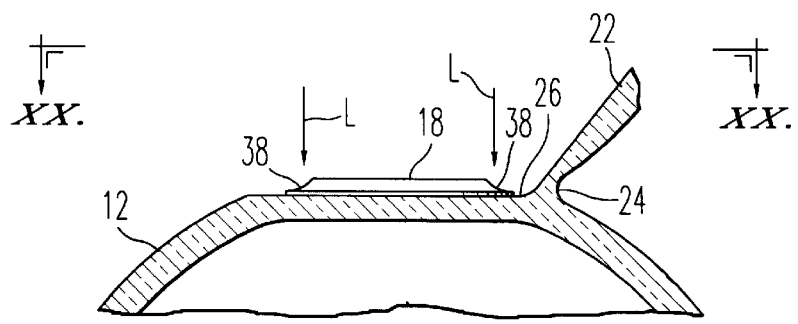
FIG. 19 is a side elevational view in section taken through the center of the eye showing ablation of the portions of the universal blank by irradiation of the laser beam as shown in FIG. 18.
Figure 20:
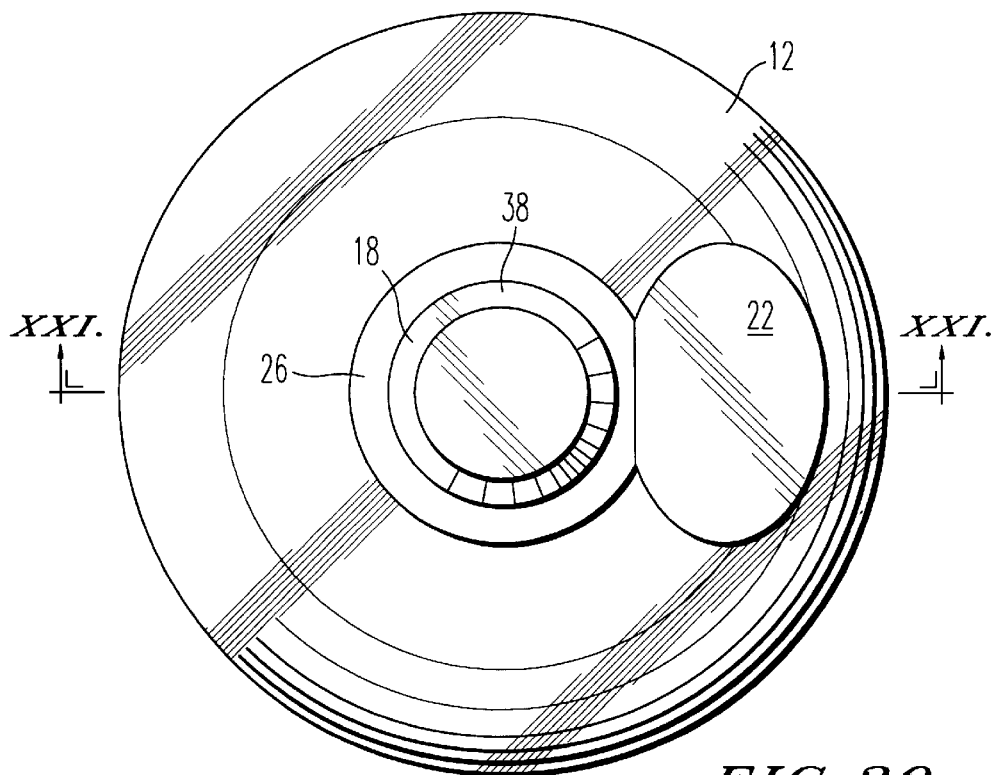
FIG. 20 is a reduced front elevational view taken along lines XX—XX in FIG. 19.
Figure 21:
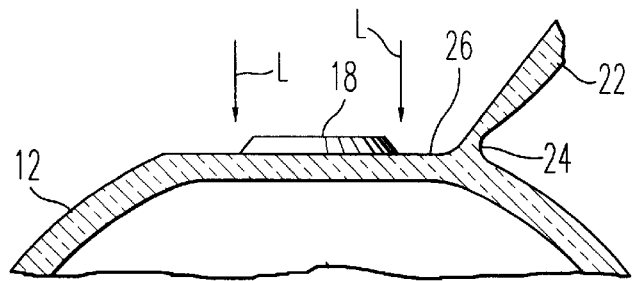
FIG. 21 is an enlarged cross-sectional view taken along lines XXI—XXI in FIG. 20.

Alternatively, if the blank 18 is being used to correct a high myopia condition, the laser beam L can be directed toward the outer perimeter of the blank as shown, for example, in FIGS. 18–21. As discussed above, the blank 18 is made of a material which will absorb all or substantially all of the laser beam. Therefore, as shown in FIG. 19 specifically, the blank 18 will be ablated by the laser beam, but none or substantially none of the surface 26 of the cornea 12 below the ablated area 38 of the blank will be ablated.

Figure 22:
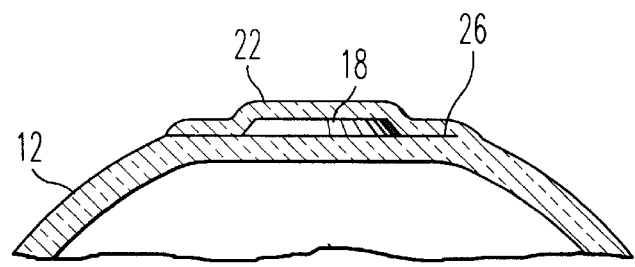
FIG. 22 is a side elevational view in section taken through the center of the eye showing the cornea and the flap-like portion reattached over the exposed surface of the cornea and the remaining portion of the universal blank ablated by the laser beam as shown in FIG. 19.

The laser beam L can be irradiated onto the ablated area 38 of the blank 18 until that area 38 is ablated down to the surface 26 of the cornea on which the blank 18 is positioned, and the remaining portion of blank 18 thus has a frustoconical shape. Of course, the blank 18 can be shaped in any manner by the laser beam L. As shown in FIG. 22, the flap-like layer 22 is then repositioned over the remaining portion of the blank 18 so that the remaining portion of the blank 18 influences the shape of the repositioned flap-like layer 22. Since the material of the blank 18 is transparent or substantially transparent to light having a wavelength in the visible light spectrum, visible light will pass through the remaining portion of the blank 18. However, because the reshaped flap-like layer 22 has a different refractive power, the flap-like layer 22 will refract the light passing therethrough differently than prior to the reshaping. Therefore, in cooperation with the lens 16 (see FIG. 1), this reshaped layer 22 will focus the light in the appropriate manner on the retina, thus correcting the ametropic condition of the eye.

Figure 23:
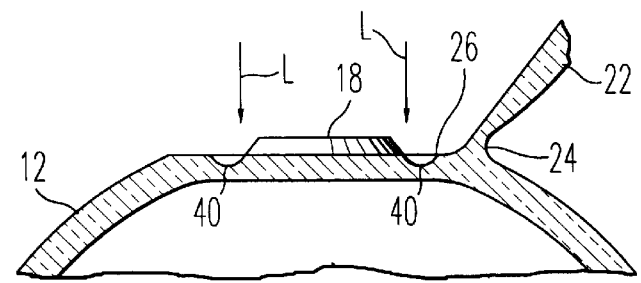
FIG. 23 is a side elevational view in section taken through the center of the eye showing ablation of portions of the universal blank and the exposed surface of the cornea below the blank by irradiation of a laser beam.
Figure 24:
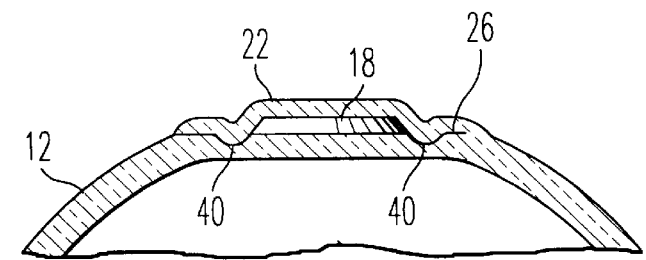
FIG. 24 is a side elevational view in section taken through the center of the eye showing the cornea and the flap-like portion reattached over the exposed surface of the cornea and the remaining portion of the universal blank as ablated by the laser beam as shown in FIG. 23.

If a more substantial modification of the shape of the cornea is necessary to correct a more severe ametropic condition, the laser beam L can be directed onto the surface 26 of the cornea 12 in order to ablate a portion 40 of that surface 26 as shown, for example, in FIG. 23. As shown in FIG. 24, when the flap-like layer is repositioned over the remaining portion of the blank 18 and the surface 26 of the cornea 12, the ablated portion 40 of the surface 26 will also influence the shape of the repositioned flap-like layer 22. Accordingly, the thickness of the blank 18 need not be increased in order to increase the degree to which the flap-like layer 22 is reshaped. High myopic conditions up to 35 diopter can be corrected by using this technique.

Figure 25:
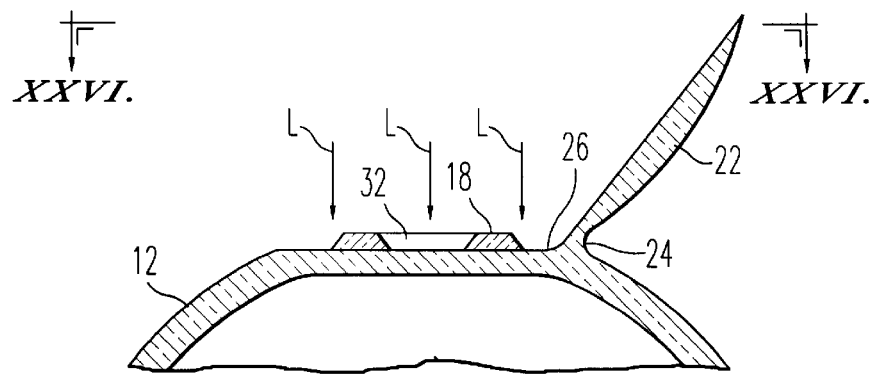
FIG. 25 is a side elevational view in section taken through the center of the eye showing ablation of multiple portions of the universal blank by irradiation of a laser beam.
Figure 26:
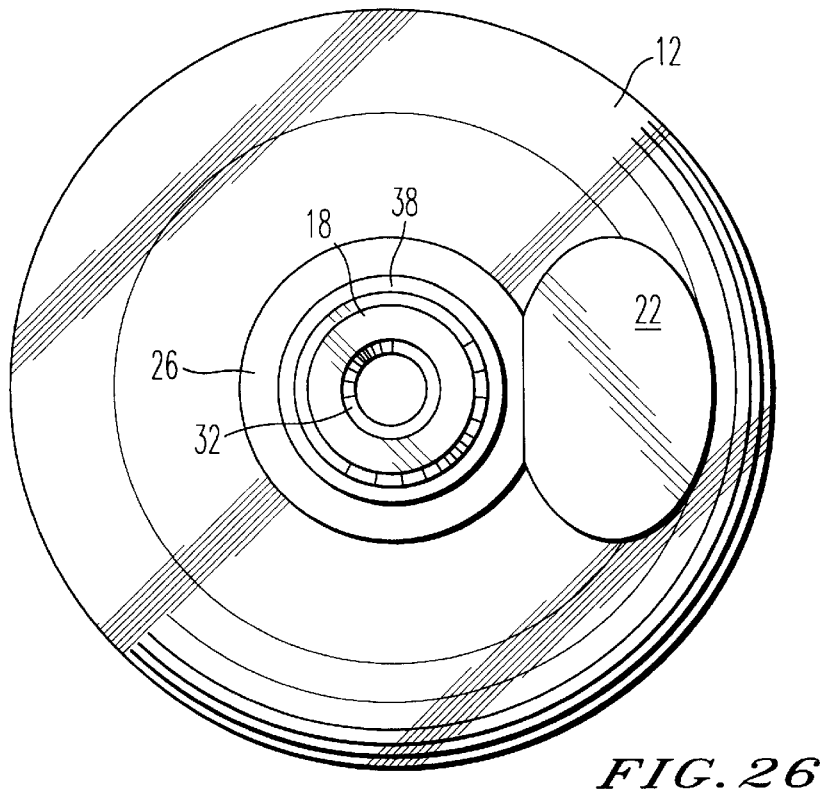
FIG. 26 is a front elevational view of the ablated universal blank taken along lines XXVI—XXVI in FIG. 25.
Figure 27:
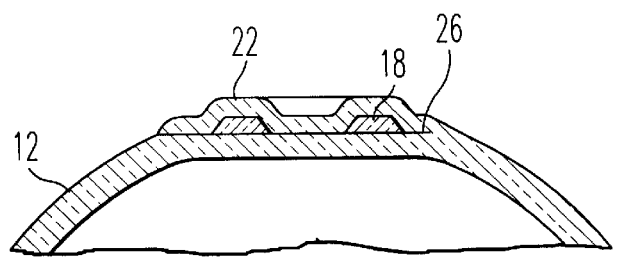
FIG. 27 is a side elevational view in section taken through the center of the eye showing the cornea and the flap-like portion reattached over the exposed surface of the cornea and the remaining portion of the universal blank ablated by the laser beam as shown in FIG. 25.

As discussed above, any portion or portions of the blank 18 can be ablated to a degree necessary to correct the ametropic condition of the eye. For example, as shown in FIGS. 25 and 26, the laser beam L can be directed toward a central area 32 of the blank 18 and also toward the portion 38 of the blank 18 to ablate inner and outer areas 32 and 38. As shown in FIG. 27, when the flap-like layer 22 is repositioned over the surface 26 of the cornea and the remaining portion of the blank 18, the remaining portion of the blank 18 will influence the shape of the flap-like layer 22.

Figure 28:
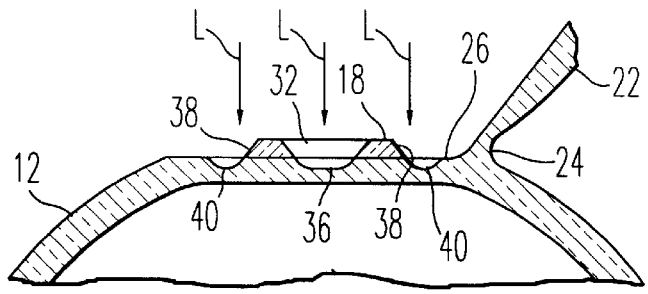
FIG. 28 is a side elevational view in section taken through the center of the eye showing ablation of multiple portions of the universal blank and cornea by irradiation of a laser beam.
Figure 29:
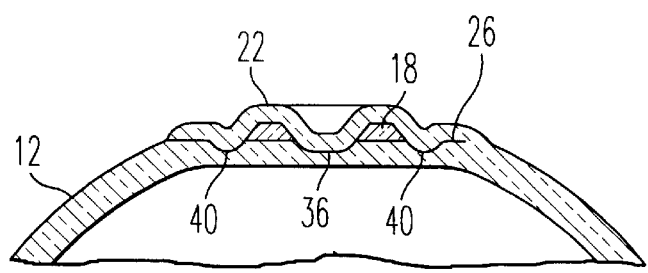
FIG. 29 is a side elevational view in section taken through the center of the eye showing the cornea and the flap-like portion reattached over the exposed surface of the cornea and the remaining portion of the universal blank as ablated by the laser beam as shown in FIG. 28.

As further shown in FIG. 28, any portion or amount of the exposed surface of the cornea 26 can be ablated as well, as long as a sufficient amount (e.g., 200 microns) of cornea is left remaining so that the remaining cornea does not experience instability or outbulging (eklasia). As illustrated, the laser beam L can be directed toward the surface 26 of the cornea underneath the ablated portions 32 and 38 of the blank 18 to ablate those portions 36 and 40 of the surface 26 of the cornea 12. Accordingly, as shown in FIG. 29, the remaining portion of the blank 18 and the ablated portions 36 and 40 of the surface 26 of the cornea 12 will influence the shape of the flap-like layer 22 when the flap-like layer 22 is repositioned over the remaining portion of the blank 18 and surface 26 of the cornea.

Figure 30:
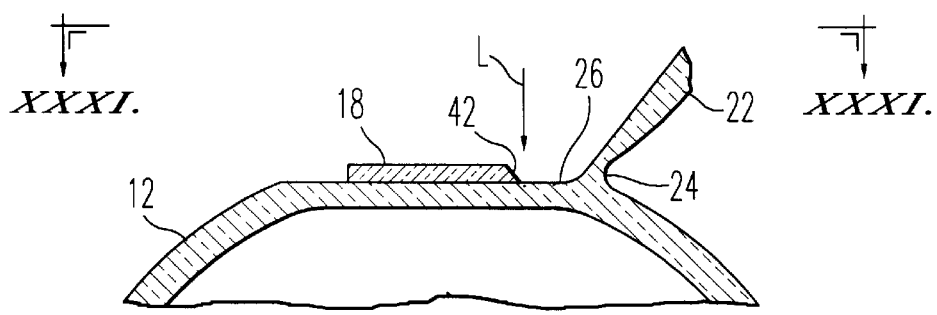
FIG. 30 is a side elevational view in section taken through the center of the eye showing ablation of the universal blank in a nonsymmetrical manner by irradiation of a laser beam.
Figure 32:
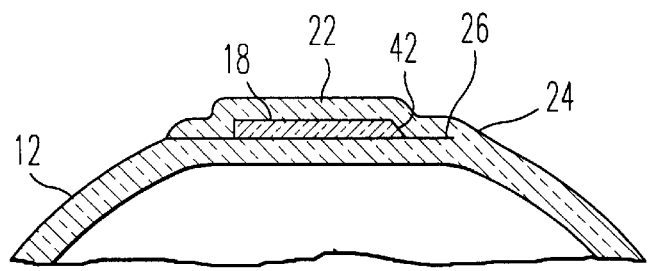
FIG. 32 is a side elevational view in section taken through the center of the eye showing the cornea and the flap-like portion reattached over the exposed surface of the cornea and the remaining portion of the universal blank as ablated by the laser beam as shown in FIG. 30.
Figure 31:
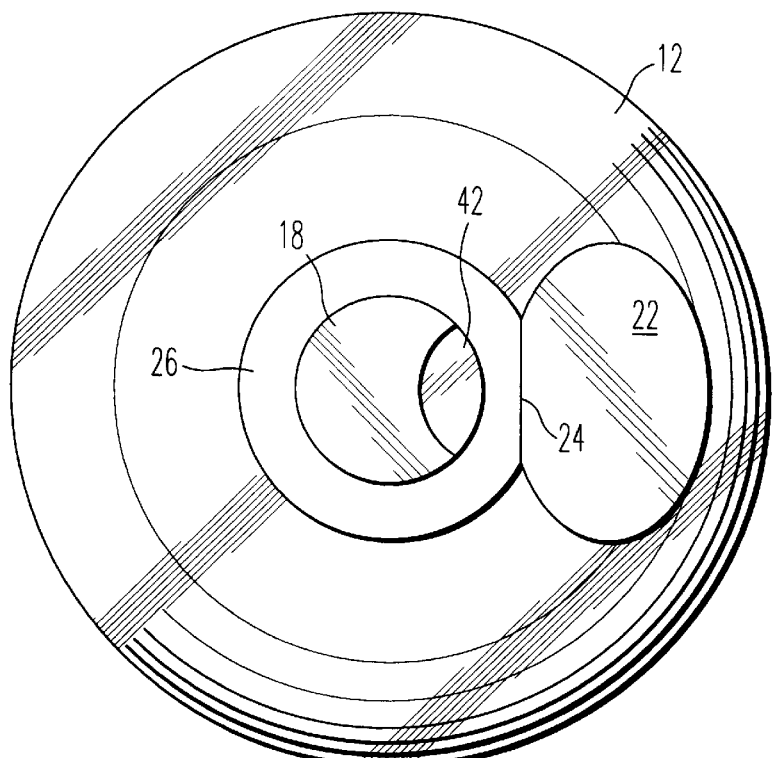
FIG. 31 is a reduced front elevational view of the ablated universal blank taken along lines XXXI—XXXI in FIG. 30.

As illustrated in FIG. 30, the laser beam L can be directed onto the blank 18 to ablate the blank in a nonsymmetrical manner. This type of shaping of the blank 18 is usually done to correct an astigmatic condition of the eye. For example, the blank can be sculpted to assume a substantially hemispherical shape resembling one-half of an egg as cut along the longitudinal axis of the eye. In other words, the blank 18 can assume a substantially hemispherical shape having a varying radius. As can be appreciated from FIG. 31, only a portion 42 of the right-side periphery of the blank 18 is ablated. Accordingly, as shown in FIG. 32, the remaining portion of the blank 18 will influence the shape of the flap-like layer 22 when the flap-like layer 22 is repositioned over the remaining portion of a blank 18 and surface of the cornea 26.

Figure 33:
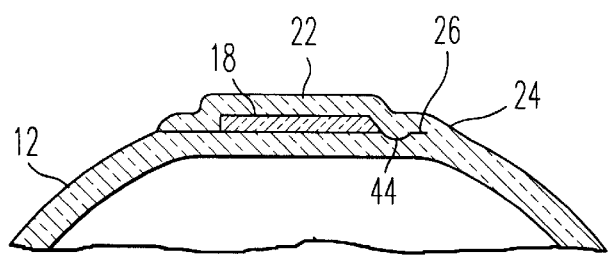
FIG. 33 is a side elevational view in section taken through the center of the eye showing the cornea and the flap-like portion reattached over the exposed surface of the cornea and the remaining portion of the universal blank after a portion of the periphery of the universal blank and a portion of the exposed surface have been ablated by a laser beam.

As shown in FIG. 33, any portion or amount of the exposed surface of the cornea 26 can be ablated in a nonsymmetrical manner as well, as long as a sufficient amount of cornea (e.g., about 200 microns) is left remaining so that the remaining cornea does not experience instability or outbulging (eklasia). In this event, the laser beam L is directed onto the portion of the disk 18 to be ablated, and after that portion has been ablated, the laser beam L is directed onto the surface of the cornea 26 below the ablated portion of the blank in a manner similar to that described, for example, with regard to FIG. 16 until a portion 44 of the surface 26 is ablated. Then, as shown in FIG. 33, the flap-like layer 22 is repositioned over the remaining portion of the blank 18 and the surface 26 of the cornea so that the remaining portion of the blank 18 and the ablated portion 44 of the surface 26 of the cornea 12 will influence the shape of the flap-like layer 22.

Figure 34:
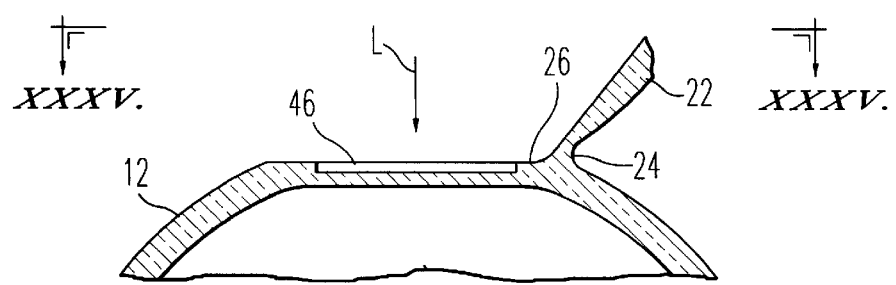
FIG. 34 is a side elevational view in section taken through the center of the eye showing a central portion of the exposed surface of the cornea being ablated by a laser beam.

FIG. 34 shows another embodiment of the method for using a universal blank according to the present invention. As illustrated, after the flap-like layer 22 has been positioned as shown in FIG. 7 to expose the inner surface 26 of the cornea, that surface 26 can be ablated by a laser beam before the blank 18 is positioned thereon. Specifically, the laser beam L is directed onto that exposed surface 26 to ablate the cornea 12 down to a particular depth. Typically, since the thickness of an average cornea is approximately 500 microns, the surface 26 can be ablated to any amount up to a depth of about 300 microns, which would leave a sufficient amount (e.g., about 200 microns) of cornea left remaining so that the cornea does not experience instability or outbulging as discussed above.

Figure 35:
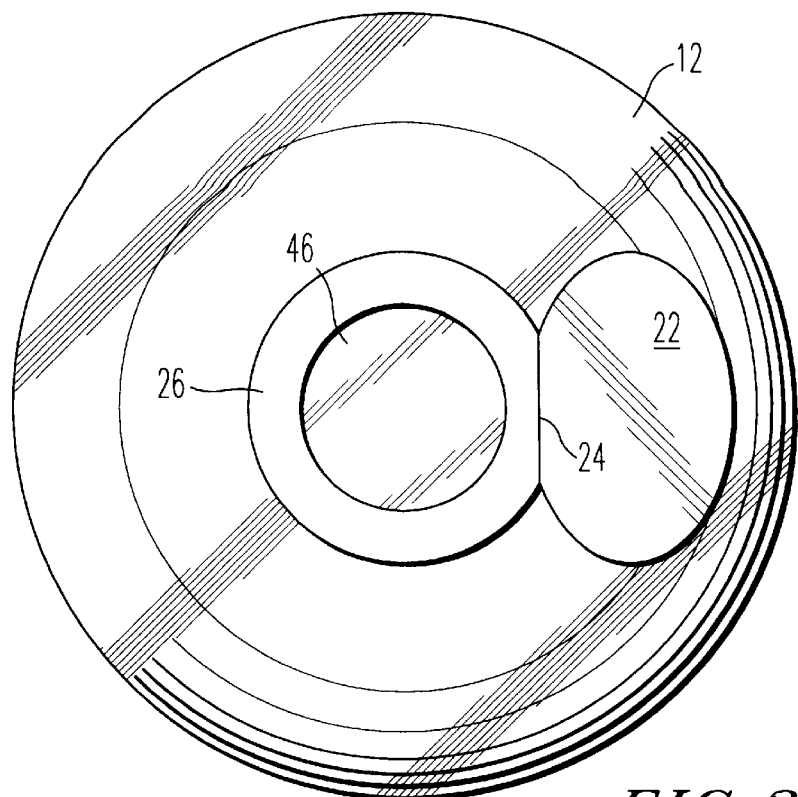
FIG. 35 is a reduced front elevational view of the ablated exposed surface of the cornea taken along lines XXXV—XXXV in FIG. 34.
Figure 36:
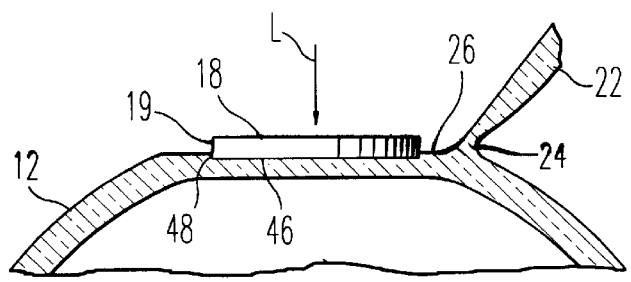
FIG. 36 is a side elevational view in section taken through the center of the eye and illustrating the universal blank shown in FIG. 2 position on the ablated exposed surface of the cornea and ablation of a central portion of the universal blank by a laser beam.

The ablated section 46 of the surface 26 can be symmetrical about the center of the front portion of the cornea as shown in FIG. 35. Preferably, the shape of the ablated section 46 will coincide with the shape of the blank 18 that is used in modifying the cornea. In the example illustrated in FIG. 36, the blank 18 is disk-shaped and hence, the ablated section 46 is circular. Furthermore, the diameter of the ablated section will coincide or substantially coincide with the diameter of the disk 18. Of course, the shape of the ablated section 46 can be asymmetrical, for example, and can vary to accommodate a disk having any shape as would be appreciative by one skilled in the art. Furthermore, the center of the ablated section need not coincide with the optical axis of the eye, but rather could be offset from the optical axis. The edge 48 of the ablated section 46 will abut against the periphery 19 of the disk as shown in FIG. 36, thereby preventing or substantially preventing the disk 18 from moving laterally on the surface 26 of the cornea. However, the edge 48 need not contact the entire periphery 19 to achieve this function.

Figure 37:
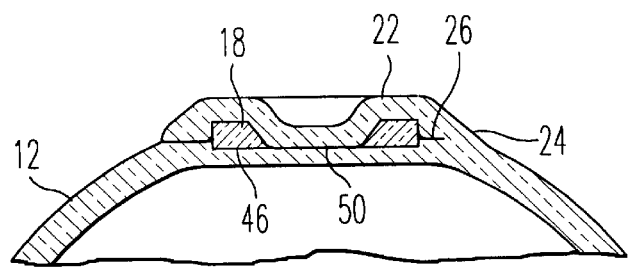
FIG. 37 is a side elevational view in section taken through the center of the eye showing the cornea and flap-like portion reattached over the exposed surface of the cornea and the remaining portion of the universal blank as ablated by the laser beam as shown in FIG. 36.

As shown in FIG. 37, the disk 18 can be ablated in the manner discussed above with regard to FIGS. 11–14 so that a recess or hole is formed in the center or substantially in the center of the blank 18. In the example shown in FIG. 37, the ablation is stopped at the exposed ablated section 46 of the surface 26 so that none or substantially none of the ablated section 46 is further ablated. The flap-like layer 22 is then repositioned over the remaining portion of the blank 18 so that the remaining portion of the blank 18 and the central portion 50 of the exposed ablated section 46 influences the shape of the repositioned flap-like layer 22.

Figure 38:
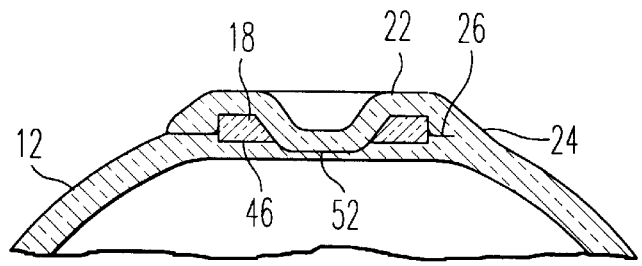
FIG. 38 is a side elevational view in section taken through the center of the eye showing the cornea and the flap-like portion reattached over the exposed surface of the cornea and the remaining portion of the universal blank after a central portion of the universal blank and a central portion of the ablated exposed surface of the cornea have been ablated by a laser beam.

Alternatively, as shown in FIG. 38, the laser beam L can be directed onto the blank 18 and the exposed ablated section 46 in a manner similar to that described above with regard to FIG. 16. By doing this, a portion 52 of the ablated section 46 of the exposed surface 26 is further ablated. The ablated section 46 can be ablated by any amount as long as a sufficient amount (e.g., about 200 microns) of cornea 12 is left remaining. In this example, the remaining portion of the blank 18 and the ablated portion 52 of the exposed ablated section 46 influences the shape of the flap-like layer 22 when the flap-like layer is repositioned over the blank 18 and the exposed surface 26 of the cornea.

Figure 39:
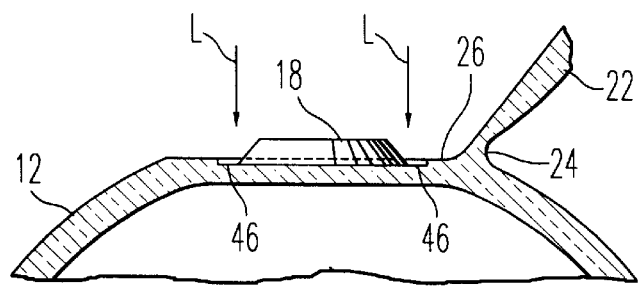
FIG. 39 is a side elevational view in section taken through the center of the eye showing ablation of peripheral portions of the universal blank which is positioned in the ablated exposed surface of the cornea.
Figure 40:
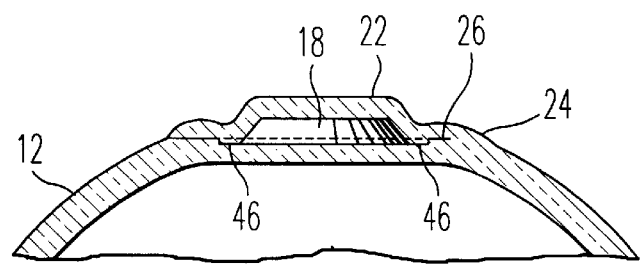
FIG. 40 is a side elevational view in section taken through the center of the eye showing the cornea and the flap-like portion reattached over the exposed surface of the cornea and remaining portion of the universal blank as ablated by the laser beam as shown in FIG. 39.
Figure 41:
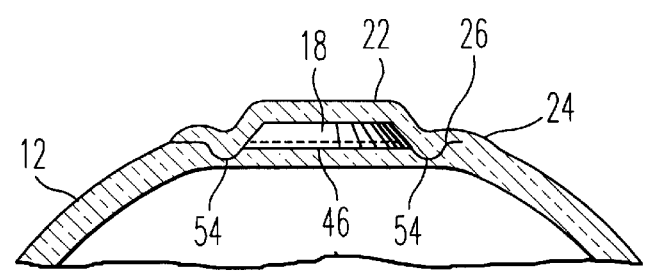
FIG. 41 is a side elevational view in section taken through the center of the eye showing the cornea and flap-like portion reattached over the exposed surface of the cornea and the remaining portion of the universal blank after the periphery of the universal blank and a portion of the ablated exposed surface of the cornea surrounding the remaining portion of the blank have been ablated by a laser beam.

As shown in FIG. 39, the periphery of the blank 18 can be ablated in the manner similar to that discussed above with regard to FIG. 21. As shown, none or substantially none of the previously ablated surface 46 of the exposed surface 26 is ablated by the laser beam. Accordingly, as shown in FIG. 40, the remaining portion of the blank 18 and the ablated section 46 of the exposed surface of the cornea influences the shape of the flap-like layer 22 when the flap-like layer is repositioned over the blank and the exposed surface 26. Alternatively, as shown in FIG. 41, a portion 54 of the ablated section 46 of the exposed surface 26 can be further ablated by the laser beam. In this event, when the flap-like layer 22 is repositioned over the exposed surface 26 and the remaining portion 18 of the blank, the ablated portion 54 and remaining portion of the blank 18 influence the shape of the flap-like layer 22.

Figure 42:
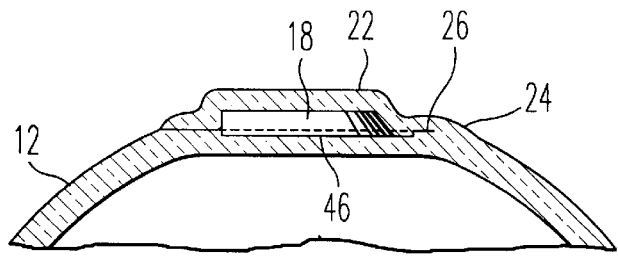
FIG. 42 is a side elevational view in section taken through the center of the eye showing the cornea and the flap-like portion reattached over the exposed surface of the cornea and a remaining portion of the universal blank which has been ablated in a nonsymmetrical manner by a laser beam.
Figure 43:
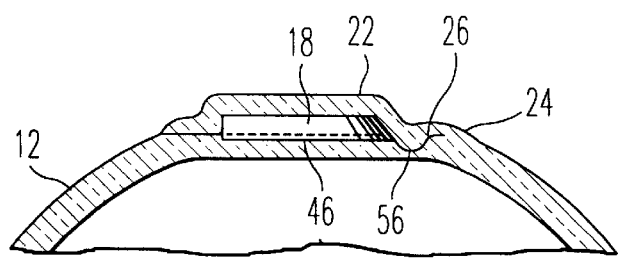
FIG. 43 is a side elevational view in section taken through the center of the eye showing the cornea and the flap-like portion reattached over the exposed surface of the cornea and the remaining portion of the universal blank after a portion of the ablated exposed surface and universal blank have been ablated by a laser beam in a nonsymmetrical manner.

As further shown in FIGS. 42 and 43, a portion of the blank 18 alone or a portion of the blank 18 and a portion 56 of the ablated section 46 of the exposed surface 26 of the cornea 12 can be ablated in a nonsymmetrical manner. Accordingly, when the flap-like layer 22 is repositioned over the exposed surface 26 and the remaining portion of the blank, the shape of the remaining portion of the blank 18 and the ablated portion 56 influence the shape of the flap-like layer 22.

Figure 44:
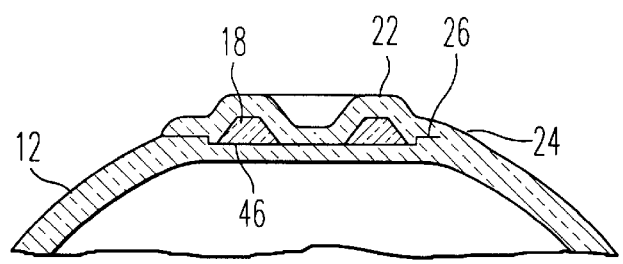
FIG. 44 is a side elevational view in section taken through the center of the eye showing the cornea and the flap-like portion reattached over the exposed surface of the cornea and the remaining portion of the universal blank of which multiple portions have been ablated by a laser beam.
Figure 45:
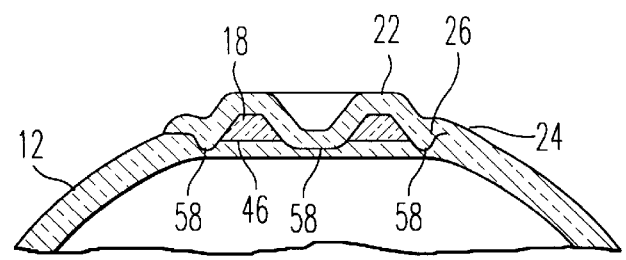
FIG. 45 is a side elevational view in section taken through the center of the eye showing the cornea and the flap-like portion reattached over the exposed surface of the cornea and the remaining portion of the universal blank after multiple portions of the ablated portion of the exposed surface and multiple portions of the universal blank have been ablated by a laser beam.

Also, as further shown in FIGS. 44 and 45, multiple portions of the blank 18 alone or multiple portions of the blank and multiple portions 58 of the ablated section 46 of the exposed surface 26 can be ablated by the laser beam. Accordingly, the remaining portion of the blank 18, and the ablated portions 58 of the ablated section 46 of the exposed surface influence the shape of the flap-like layer 22 when the flap-like layer is repositioned over the remaining portion of the blank 18 and the exposed surface 26.

Figure 46:
FIG. 46 is a perspective view of another embodiment of a universal blank according to the present invention.
Figure 47:
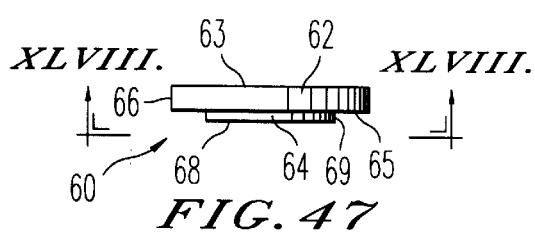
FIG. 47 is a front view of the embodiment shown in FIG. 46.
Figure 48:
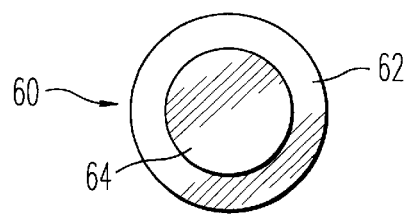
FIG. 48 is a bottom view of the embodiment shown in FIG. 46 as taken along lines XLVIII—XLVIII in FIG. 47.

Another embodiment of the universal blank according to the present invention is shown in FIGS. 46–48. Specifically, the blank 60 shown in FIG. 46 has a large portion 62 and a small portion 64. The large portion 62 can have any practical size and shape as could the blank 18 shown in FIG. 2 as discussed above, and can be made of the same type of materials as the blank 18.

In the example shown in FIG. 46, the large portion 62 of the blank 60 is disk-shaped and has a diameter of about 4 to about 9 millimeters and a thickness of between about 20 and about 500 microns. Of course, the diameter and thickness of the blank 60 can be of any practical size that would be appreciated by one skilled in the art.

As further illustrated in FIGS. 47 and 48, the small portion 64 of the blank 60 is also disk-shaped, but has a small diameter than the large portion 62. The diameter of small portion 64 can be any practical size, such as a small disk-shaped projection having a nominal diameter up to a disk-shaped projection having a diameter only a fraction smaller than the diameter of the large shaped portion 62. Of course, the small portion 64 need not be disk-shaped, but can have any practical shape as would be appreciative by one skilled in the art. Furthermore, the large portion 62 and small portion 64 can have shapes different from each other. Hence, for example, the large portion 62 can be disk-shaped while the small portion 64 can be oval or rectangularly shaped.

The large portion 62 has a first planar or substantially planar surface 63, a second planar or substantially planar surface 65, and a periphery 66. The surfaces 63 and 65 can be parallel or substantially parallel to each other, and the periphery 66 can be perpendicular to one or both of the surfaces 63 and 65. Of course, the surfaces 63 and 65 and the periphery 66 need not be smooth but can have projected portions, recesses or any type of texture.

The small portion 64 is integral with or attachable to the large portion 62 and a planar or substantially surface 68 and a periphery 69. The surface 68 can be parallel or substantially parallel to one or both of the surfaces 63 and 65 of the large portion 62, and the periphery 69 could be perpendicular or substantially perpendicular to the surface 68. Of course, the surface 68 and periphery 69 need not be smooth but can have projected portions, recesses or any type of texture.

Figure 49:
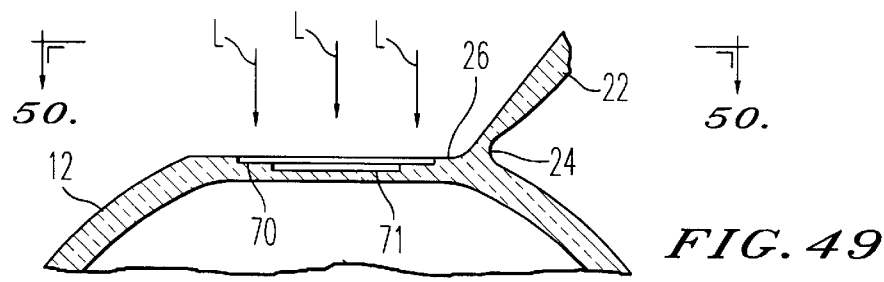
FIG. 49 is a side elevational view in section taken through the center of the eye showing ablation of the exposed surface of the cornea by a laser beam to different depths.
Figure 50:
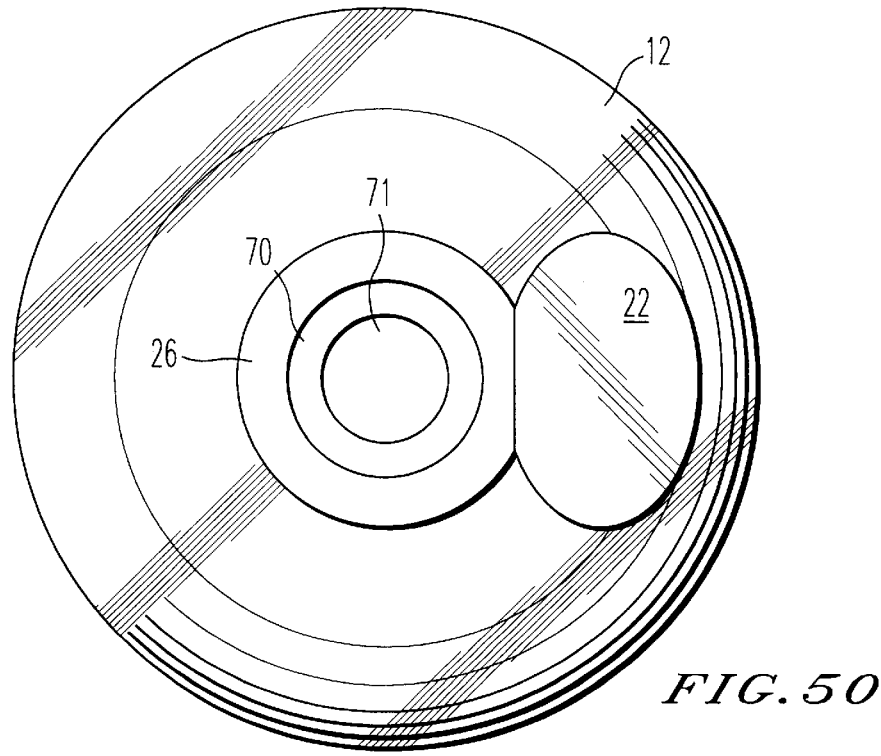
FIG. 50 is a reduced front view of the cornea as taken along lines 50—50 in FIG. 49.

An embodiment of a method for using the universal blank 60 according to the present invention is shown in FIG. 49. Specifically, the surface of the cornea 26 that has been exposed by forming and positioning the flap-like layer 22 in the manner discussed above is ablated in the manner shown in FIG. 49. That is, the exposed surface 26 is ablated to different depths so as to assume a shape which can accommodate the blank 60. Hence, an outer section 70 of the exposed surface 26 is ablated to a first depth, while an inner section 71 is ablated to a second depth greater than the first depth. The depths of the ablated inner and outer sections 70 and 71 can be any amount which would allow a sufficient amount of cornea 12 (e.g., about 200 microns) to remain so that the remaining cornea does not experiencing distortion or outbulging. It is noted that this step-shaped blank 60 provides an advantage over a uniformly shaped blank 18 in this regard, because less volume of cornea can be ablated to form a recess which will accommodate the smaller portion 64 of the blank 60 and thus point the blank 60 from shifting on the surface of the cornea. That is, the volume of cornea removed to form section 71 is less than the volume of cornea removed to form section 46 (FIG. 34).

Figure 51:
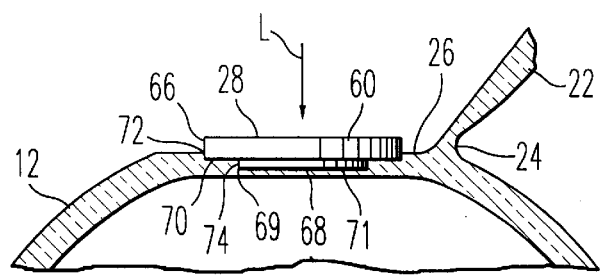
FIG. 51 is a side elevational view in section taken through the center of the eye showing the universal blank illustrated in FIG. 46 positioned on the exposed surface of the cornea after the exposed surface has been ablated as shown in FIG. 49.

As shown in FIG. 51, the blank 60 is positioned on the ablated sections 70 and 71 of the exposed surface 26 so that the surface 68 of the small portion 64 of the blank 60 contacts or substantially contacts the ablated section 71 while the surface 65 of the large portion 62 of the blank 60 contacts or substantially contacts the ablated section 70 as shown. As further shown, an edge 72 of the ablated section 71 contacts the periphery 66 of the large portion of the blank 60, while an edge 74 of the ablated section 71 contacts the periphery 69 of the small portion 64 of the blank 60. Of course, the sizes and shapes of the ablated section 70 and 71 can be made to conform or substantially conform with the sizes and shapes of the large and small portions 62 and 64, respectively, of the blank 60, and can thus be any practical size and shape as would be appreciated by one skilled in the art. Also, the ablated sections 70 and 71 need not be made symmetrical about the central optical axis of the eye, but rather, could be offset from the central optical axis of the eye and from each other. The edges 72 and 74 of the ablated sections 70 and 71, respectively, can contact the peripheries 66 and 69, respectively, in their entirety or at various locations.

Figure 52:
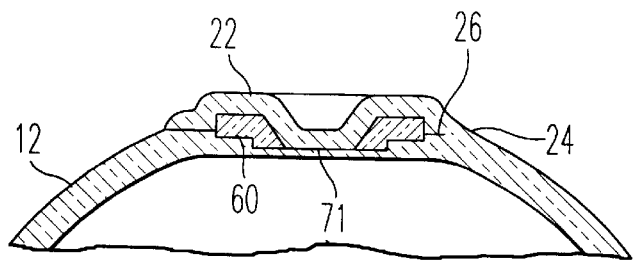
FIG. 52 is a side elevational view in section taken through the center of the eye showing the cornea and the flap-like portion reattached over the exposed surface of the cornea and the remaining portion of the universal blank illustrated in FIG. 46 as ablated by the laser beam as shown in FIG. 51.

As further shown in FIG. 51, the laser beam L is irradiated onto the blank 60 in a manner similar to that described above with regard to FIGS. 11–14 to ablate a central or substantially central portion of the blank 60 as shown in FIG. 52. That ablated portion can be, for example, a substantially hemispherical recess as discussed above with regard to FIGS. 11–14. As further shown in FIG. 52, none or substantially none of the ablated section 71 is further ablated by this laser beam. Accordingly, the surface of the ablated section 71 and the remaining portion of the blank 60 influence the shape of the flap-like layer 22 when the flap-like layer 22 is repositioned over the blank 60 and the exposed surface 26.

Figure 53:
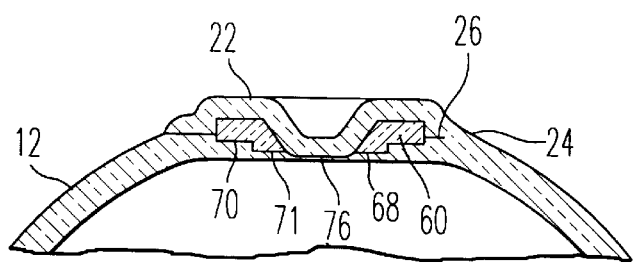
FIG. 53 is a side elevational view in section taken through the center of the eye showing the cornea and the flap-like portion reattached over the exposed surface of the cornea and the remaining portion of the universal blank shown in FIG. 46 after a central portion of the universal blank and a central portion of the ablated exposed surface of the cornea have been ablated by a laser beam.

Alternatively, shown in FIG. 53, a portion 76 of the ablated section 71 below the ablated portion of the blank 60 can be further ablated by the laser beam to any depth which would allow a sufficient amount (e.g., about 200 microns) of the cornea 12 to remain. Accordingly, the ablated portion 76 and remaining portion of the blank 60 influence the shape of the flap-like layer 22 when the flap-like layer 22 is repositioned back over the exposed surface 26 and the remaining portion of the disk 60.

Figure 54:
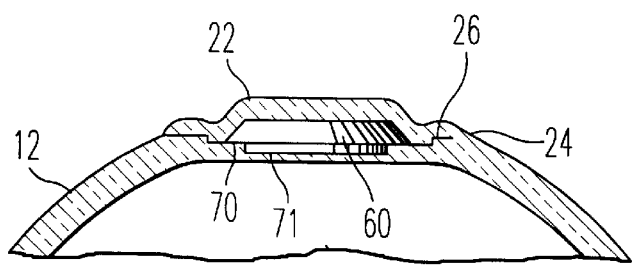
FIG. 54 is a side elevational view in section taken through the center of the eye showing the cornea and the flap-like portion reattached over the exposed surface of the cornea and the remaining portion of the universal blank shown in FIG. 46 whose periphery has been ablated by a laser beam.
Figure 55:
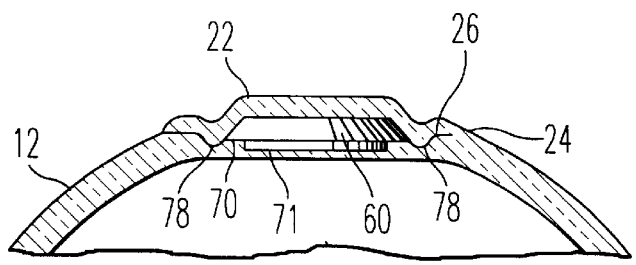
FIG. 55 is a side elevational view in section taken through the center of the eye showing the cornea and the flap-like portion reattached over the exposed surface of the cornea and the remaining portion of the universal blank after a portion of the periphery of the universal blank and a portion of the ablated exposed surface surrounding the remaining portion of the blank have been ablated by a laser beam.

As further shown in FIG. 54, multiple portion of the blank 60 can be ablated in a manner similar to that in which the blank 18 is ablated as described, for example, with respect to FIGS. 18–22 above. Furthermore, as shown in FIG. 55, the laser beam can be directed onto the ablated section 70 of the exposed surface 26 to ablate portion 78 of that ablated section 70. Accordingly, as shown in FIG. 54, the remaining portion of the blank 60 and the ablated section 70 influence the shape of the flap-like layer 22 when the flap-like layer 22 is repositioned over the exposed surface 26 and the remaining portion of the blank 60. Conversely, as shown in FIG. 55, the remaining portion of the blank 60 and the further ablated portion 78 of the ablated section 70 of the exposed surface 26 influence the shape of the flap-like layer 22 when the flap-like layer 22 is repositioned over the exposed surface 26 in the remaining portion of the blank 60.

Figure 56:
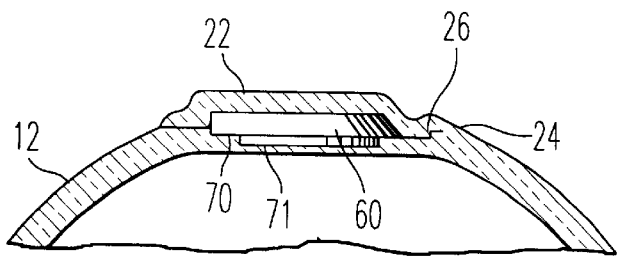
FIG. 56 is a side elevational view in section taken through the center of the eye showing the cornea and the flap-like portion reattached over the exposed surface of the cornea and the remaining portion of the universal blank shown in FIG. 46 which has been ablated by the laser beam in a nonsymmetrical manner.
Figure 57:
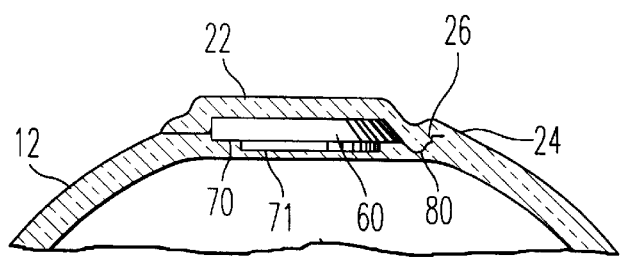
FIG. 57 is a side elevational view in section taken through the center of the eye showing the cornea and the flap-like portion reattached over the exposed surface of the cornea and the remaining portion of the universal blank shown in FIG. 46 after a portion of the universal blank and a portion of the ablated exposed surface have been ablated by the laser beam in a nonsymmetrical fashion.

As further shown in FIGS. 56 and 57, the blank 60 and ablated section 70 of the exposed surface 26 can be ablated by the laser beam in a nonsymmetrical manner. Accordingly, as shown in FIG. 56, the remaining portion of the blank 60 and the ablated section 70 influence the shape of the flap-like layer 22 when the flap-like layer is repositioned over the surface 26 in the remaining portion of the blank 60. As shown in FIG. 57, the nonsymmetrical ablated portion 80 and the remaining portion of the blank 60 influence the shape of the flap-like layer 22 when the flap-like layer is repositioned over the exposed surface 26 and the remaining portion of the blank 60.

Figure 58:
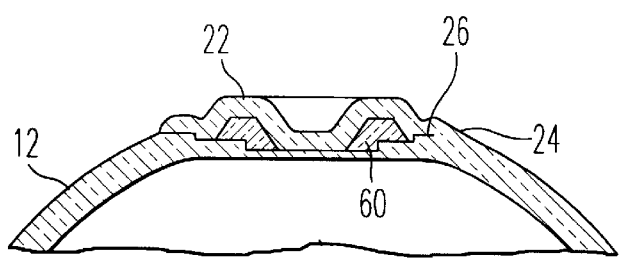
FIG. 58 is a side elevational view in section taken through the center of the eye showing the cornea and the flap-like portion reattached over the exposed surface of the cornea and the remaining portion of the universal blank shown in FIG. 46 of which multiple portions have been by a laser beam.
Figure 59:
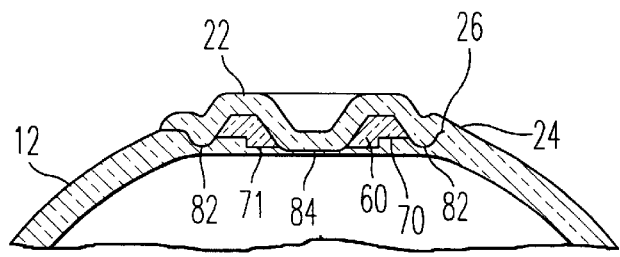
FIG. 59 is a side elevational view in section taken through the center of the eye showing the cornea and the flap-like portion reattached over the exposed surface of the cornea and the remaining portion of the universal blank shown in FIG. 46 after multiple portions of the universal blank and multiple portions of the ablated exposed surface have been ablated by the laser beam.

As shown in FIGS. 58 and 59, the blank 60 and ablated section 70 can be ablated at multiple locations in a manner similar to that in which the blank 18 and surface 26 are ablated as described above with regard to FIGS. 25–29. Accordingly, as shown in FIG. 58, the remaining portion of the blank 60 and the ablated sections 70 and 71 of the exposed surface 26 influence the shape of the flap-like layer 22 when the flap-like layer 22 is repositioned over the exposed surface 26 and the blank 60. Alternatively, as shown in FIG. 59, the further ablated portion 82 of the ablated section 70, the further ablated portion 84 of the ablated section 71, and the remaining portion of the blank 60 influence the shape of the flap-like layer 22 when the flap-like layer 22 is repositioned over the remaining portion blank 60 and the exposed surface 26.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. A blank, adaptable for use in modifying the curvature of a patient's live cornea, comprising:
    a first surface adapted for placement directly on a substantially flat surface of said patient's live cornea, and being conformable with said substantially flat surface;
    a second surface, opposite said first surface, adapted to be exposed to a laser beam and including a planar portion;
    said blank comprising a material whose properties permit light having a wavelength within the visible spectrum to pass therethrough and prevent substantially all light having a wavelength within the laser light spectrum from passing therethrough, and having a thickness at a perimeter thereof sufficient to substantially prevent said laser beam from ablating said substantially flat surface of said patient's live cornea located below said perimeter.

2. A blank according to claim 1, wherein said material is adapted to be ablated by laser light.

3. A blank according to claim 1, wherein said thickness of said blank is within a range of about 20 to about 500 microns, and a length of at least one of said first and second surfaces of said blank is within a range of about 2 mm to about 9 mm.

4. A blank according to claim 1, wherein said blank is a disk having said first and second surfaces on opposite sides thereof, said thickness of said blank is within a range of about 20 to about 500 microns, and the diameter of said blank is within a range of about 2 mm to about 9 mm.

5. A blank according to claim 1, wherein said material is one of organic material and synthetic material.

6. A blank according to claim 1, wherein said material is one of collagen, copolymer collagen, polyethylene oxide and hydrogel.

7. A blank according to claim 1, wherein said material includes one of the following cross-linked organic materials: collagen, hyaluronic acid, mucopolysaccharide and glycoprotein.

8. A blank according to claim 1, wherein said blank has a substantially uniform thickness between said first and second surfaces.

9. A blank according to claim 1, wherein said first and second surfaces each are substantially planar surfaces.

10. A blank according to claim 9, wherein said first and second surfaces are substantially parallel to each other.

11. A blank according to claim 1, further comprising a third surface extending between said first and second surfaces substantially normal to said planar portion, and having a length equal to said thickness.

12. A blank, adaptable for use in modifying the curvature of a patient's live cornea, comprising:
    a first portion having a first surface adapted for placement directly on a substantially flat surface of said patient's live cornea, and being conformable with said substantially flat surface;
    a second portion, integral with and longer than said first portion, and having a second surface adapted for placement directly on a substantially flat surface of said patient's live cornea, and a third surface, opposite said second surface, adapted to be exposed to a laser beam, said third surface including a substantially planar portion
    said blank comprising a material whose properties permit light having a wavelength within the visible spectrum to pass therethrough and prevent substantially all light having a wavelength within the laser light spectrum from passing therethrough, and the second portion having a thickness at a perimeter thereof sufficient to substantially prevent said laser beam from ablating said substantially flat surface of said patient's live cornea located below said perimeter.

13. A blank according to claim 12, wherein said first and third surfaces are each substantially planar.

14. A blank according to claim 13, wherein said first and third surfaces are substantially parallel to each other.

15. A blank according to claim 12, wherein said second portion further includes a fourth surface, extending between said second and third surfaces substantially normal to said planar portion, and having a length equal to said thickness.

16. A blank according to claim 12, wherein said first, second and third surfaces are each substantially planar.

17. A blank according to claim 16, wherein said first, second and third surfaces are substantially parallel to each other.

18. A blank according to claim 12, wherein said second portion further comprises a fourth surface, extending between said second and third surfaces substantially normal to said planar portion.

19. A blank according to claim 12, wherein said first portion further comprises a fifth surface, extending between said first and second surfaces substantially parallel to said fourth surface.

20. A blank according to claim 12, wherein said first and second portions are each cylindrically shaped, with the diameter of the second portion being greater than the diameter of the first portion.

* * * * *